United States Patent
Amon et al.

(10) Patent No.: US 10,814,104 B2
(45) Date of Patent: Oct. 27, 2020

(54) RETENTION MEMBER FOR SECURING A CATHETER ON A PATIENT

(71) Applicant: Fresenius Kabi Deutschland GmbH, Bad Homburg (DE)

(72) Inventors: Barbara Amon, Idstein (DE); Benjamin Schäfer, Hohenahr (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 184 days.

(21) Appl. No.: 16/069,578

(22) PCT Filed: Jan. 10, 2017

(86) PCT No.: PCT/EP2017/050371
§ 371 (c)(1),
(2) Date: Jul. 12, 2018

(87) PCT Pub. No.: WO2017/121709
PCT Pub. Date: Jul. 20, 2017

(65) Prior Publication Data
US 2019/0224453 A1    Jul. 25, 2019

(30) Foreign Application Priority Data
Jan. 13, 2016   (EP) .................................. 16151052

(51) Int. Cl.
*A61M 5/32* (2006.01)
*A61M 25/02* (2006.01)

(52) U.S. Cl.
CPC ....... *A61M 25/02* (2013.01); *A61M 2025/026* (2013.01); *A61M 2025/028* (2013.01); *A61M 2025/0253* (2013.01)

(58) Field of Classification Search
CPC .... A61M 2025/0253; A61M 2025/026; A61M 2025/028; A61M 25/02
See application file for complete search history.

(56) References Cited

U.S. PATENT DOCUMENTS

| | | |
|---|---|---|
| 4,088,136 A | 5/1978 | Hasslinger et al. |
| 4,198,989 A | 4/1980 | Hawke et al. |

(Continued)

FOREIGN PATENT DOCUMENTS

| | | |
|---|---|---|
| CN | 104039379 A | 9/2014 |
| CN | 104602728 A | 5/2015 |

(Continued)

OTHER PUBLICATIONS

International Search Report and Written Opinion, counterpart International Appl. No. PCT/EP2017/050371, dated Apr. 10, 2017 (16 pages).

(Continued)

*Primary Examiner* — Rebecca E Eisenberg
(74) *Attorney, Agent, or Firm* — Cook Alex Ltd.

(57) ABSTRACT

A retention member (1) for securing a catheter (2) on a patient (P) comprises a base element (10) having a bottom side (103) and a top side (104), the bottom side being placeable on the patient (P) and the top side (104) being adapted for receiving the catheter (2). The retention member (1) furthermore comprises a ribbon (14) having a first end (140) connected to the top side (104) of the base element (10) and having a second end (141) opposite the first end (140), wherein the base element (10) comprises at least one opening (150, 151) through which the second end (141) of the ribbon (14) is insertable for fixing the catheter (2) on the retention member (1) in between the base element (10) and the ribbon (14). In this way a retention member is provided which is easy and safe to use, may suit to secure catheters of different sizes on a patient and at the same time may be manufactured in a cost-effective manner.

20 Claims, 5 Drawing Sheets

(56) References Cited

U.S. PATENT DOCUMENTS

| | | | |
|---|---|---|---|
| 5,395,343 A | | 3/1995 | Iscovich |
| 5,527,293 A | | 6/1996 | Zamierowski |
| 5,683,403 A | * | 11/1997 | Adams .................. A61B 17/08 |
| | | | 604/174 |
| 2008/0249476 A1 | * | 10/2008 | Bierman ............... A61M 25/02 |
| | | | 604/175 |
| 2012/0277682 A1 | | 11/2012 | Corato et al. |
| 2013/0165863 A1 | * | 6/2013 | Nilson .................. A61M 25/02 |
| | | | 604/180 |

FOREIGN PATENT DOCUMENTS

| | | |
|---|---|---|
| CN | 104602729 A | 5/2015 |
| EP | 0 574 163 A1 | 12/1993 |
| EP | 1 698 368 A1 | 9/2006 |
| EP | 2 833 497 A2 | 2/2015 |

OTHER PUBLICATIONS

English-language translation of Chinese Search Report for corresponding Chinese application No. 201780006754.X, dated Jun. 18, 2020 (2 pages).

English-language translation of Chinese First Office Action for corresponding Chinese application No. 201780006754.X, dated Jun. 24, 2020 (8 pages).

\* cited by examiner

RETENTION MEMBER FOR SECURING A CATHETER ON A PATIENT

The invention relates to a retention member for securing a catheter on a patient according to the preamble of claim 1.

A retention member of this kind comprises a base element having a bottom side and a top side, the bottom side being placeable on the patient's skin and the top side being adapted for receiving the catheter.

A retention member for securing a catheter on a patient known from US 2008/0132848 A1 comprises a base element forming a receiving structure into which a catheter fitting is insertable. By fixing a cover to the base element the catheter can be secured on the base element and in this way can be fixedly arranged on the patient.

U.S. Pat. No. 5,137,519 describes a retention element defining a tubular member having a bore for receiving and retaining a catheter therein.

A retention member of the kind concerned herein may for example be used to secure a catheter for the medication, hydration or feeding of a patient. A catheter of this kind may for example be used to access the gastro-intestinal tract of the patient, for example for the intra-gastric feeding of the patient.

Generally, for the feeding of a patient or for other applications catheters of different kinds may be used. Conventional retention members herein are adapted for a catheter of a particular diameter and a particular material, such that for different catheters different retention members must be selected, a wrong selection leading potentially to an incomplete securing of a catheter on the patient. In addition, having to provide different retention members for different catheters increases the logistic expenditure and the manufacturing costs.

One requirement for a retention member is for example a safe and reliable fixation of a catheter under tensile to build a stoma channel during the first hours after a catheter placement. A retention member shall be usable over a longer time period, over hours or days, and shall be easy to handle in daily use for a user, for example a nurse.

It is an object of the instant invention to provide a retention member which is easy and safe to use, may suit to secure catheters of different sizes on a patient and at the same time may be manufactured in a cost-effective manner.

This object is achieved by means of a retention member comprising the features of claim 1.

Accordingly, the retention member comprises a ribbon having a first end connected to the top side of the base element and having a second end opposite the first end, wherein the base element comprises at least one opening through which the second end of the ribbon is insertable for fixing the catheter on the retention member in between the base element and the ribbon.

The retention member may for example be integrally formed in one piece. The retention member may for example be made from silicone rubber.

The retention member allows securing a catheter on a patient by fastening the catheter by means of the ribbon on the base element of the retention member. The ribbon comprises a first end connected to the top side of the base element and a second end opposite the first end. With the second end the ribbon can be inserted through an opening of the base element such that a loophole is formed through which the catheter can be inserted such that the catheter is held on the base element by means of the ribbon extending circumferentially about the catheter.

The base element, in one embodiment, comprises a first opening and a second opening separated from each other by a rib. The ribbon can be inserted through the first opening and the second opening such that it extends through the first opening from the top side of the base element towards the bottom side, reaches around the rib and extends through the second opening of the base element from the bottom side towards the top side. Hence, in the inserted state the ribbon, with its second end, projects from the top side of the base element such that a user can pull on the second end for securing a catheter to the base element. By extending about the rib the ribbon is deformed and is securely fastened to the base element such that a catheter placed in the loophole formed by the ribbon is securely held on the base element and, by placing the base element with its bottom side on a patient, can be secured on the patient.

The rib may, in one embodiment, be recessed at a side opposite the top side of the base element with respect to the bottom side of the base element. The bottom side of the rib hence is displaced with respect to the bottom side of the base element towards the inside, allowing to place the ribbon around the rib without the ribbon protruding beyond the bottom side of the base element. This allows to for example tape the base element to the skin of the patient in an easy, reliable manner.

On the top side of the base element, in one embodiment, an elevation is placed, the elevation extending along the rib in between the first opening and the second opening and protruding from the top side of the base element. By means of the elevation the base element may be stiffened in the region of the rib such that the ribbon can be securely fastened to the base element by inserting the ribbon with its second end through the first and the second opening to extend about the rib formed in between the first opening and the second opening.

The base element, in one embodiment, has a generally triangular shape, wherein the base element may be rounded at its tips. The ribbon may be placed at a central location on the base element such that a catheter may be placed on the top side of the base element to extend along a middle line from a leg in between a first tip and a second tip of the triangular base element towards a third tip of the base element.

To receive the catheter on the base element, a groove may be formed into the top side of the base element. The ribbon in this case is connected with its first end to the top side of the base element such that the ribbon bridges over the groove when inserted into the at least one opening formed in the base element.

In one embodiment, the base element comprises a guide hole extending through the base element from the top side to the bottom side. The guide hole is adapted to receive the catheter, the catheter being insertable through the guide hole.

The guide hole may for example be arranged at a tip of the generally triangular base element, wherein the base element at least to some extent can be bent at the tip carrying the guide hole. When received on the base element, the catheter extends along the top side of the base element and is secured to the top side by means of the ribbon, and is inserted through the guide hole such that it extends from the top side towards the bottom side of the base element. This causes the catheter to be pressed against the skin of the patient when the retention member is placed on the patient, the catheter being tensioned towards the skin and hence assuming a defined position on the patient.

The guide hole for example may have a circular or a triangular shape. In another embodiment the guide hole may have the shape of a cross adapted to guide catheters having a fairly large diameter as well as catheters having a fairly small diameter.

In one embodiment, for example a wall section is placed on the top side of the base element, the wall section extending transversely across the top side. The wall section separates the base element, at its top side, into two regions, the guide hole being placed on a first side of the wall section and the ribbon on another, second side of the wall section. The wall section may serve to increase the stiffness of the base element along the transverse direction, such that a bending of the base element is primarily possible about the wall section, the wall section hence forming a bending axis.

In order to place the catheter on the base element to extend from the second side of the wall section (at which it is fixed to the base element by means of the ribbon) towards the first side (where the guide hole is placed), in one embodiment an opening is formed in the wall section, the opening forming a passage in the wall section for the catheter through which the catheter may extend. The catheter hence runs along the top side of the base element through the opening of the wall section and through the guide hole, hence extending from the top side of the base element to the bottom side of the base element.

In one embodiment, the ribbon comprises a reception groove formed by a curvature of the ribbon. The reception groove is adapted to receive the catheter such that, when the ribbon is inserted through the at least one opening of the base element, a beneficial seat for the catheter on the base element is provided. The reception groove herein is formed by suitably curving the ribbon, the reception groove being present in the ribbon already when the ribbon is in a relaxed state in which it is not inserted into the at least one opening of the base element.

For securing the catheter on the retention member and, via the retention member, on a patient, the ribbon is inserted through the at least one opening of the base element and, by pulling on the second end of the ribbon, the catheter is fastened on the base element. If the catheter shall be released from the retention member, a user may grab on a pulling handle, which, in one embodiment, is placed on a section of the ribbon in between the first end and the second end. By grabbing on the pulling handle, hence, a user can pull the ribbon out of the at least one opening formed in the base element and hence may open the loophole formed by the ribbon on the base element such that the catheter may be removed from the retention element.

The idea underlying the invention shall subsequently be described in more detail with respect to the embodiments shown in the figures. Herein:

Figure 1:
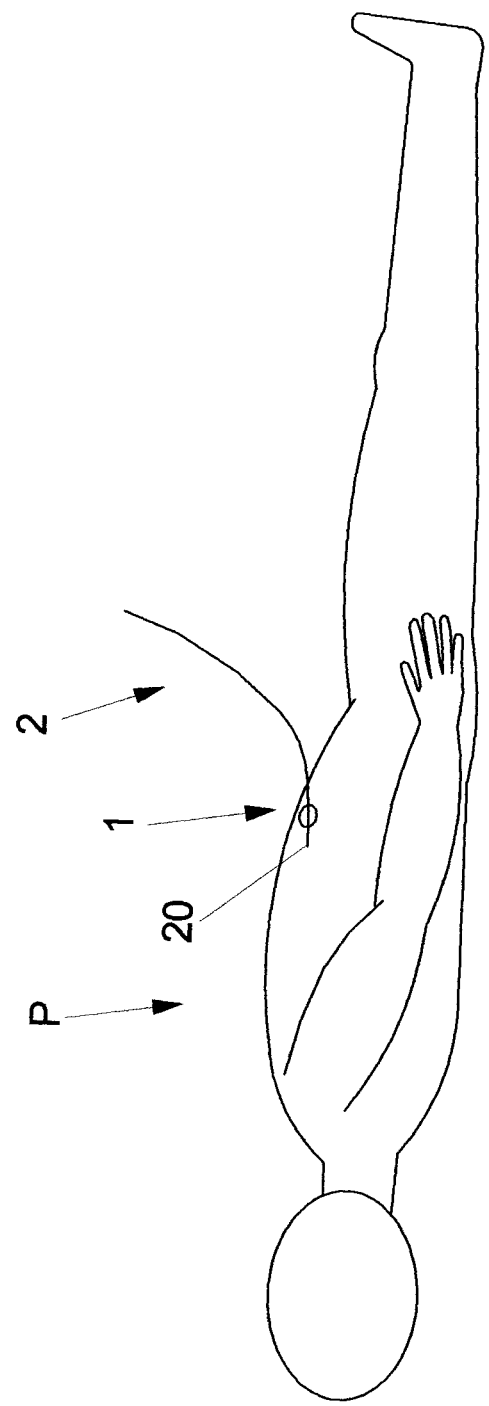
FIG. 1 shows a schematic view of a patient, a catheter being placed on the patient.

FIG. 1 shows in a schematic embodiment a general scenario of a patient P being subjected for example to a gastro-intestinal feeding. A catheter 2 is placed on the patient P, entering into the patient P through an access 20, wherein the catheter 2 is secured to the patient P close to the access 20 by means of a retention member 1 in order to avoid, for example, an accidental removal or displacement of the catheter 2.

An embodiment of a retention member 1 is shown in FIG. 2 to 5A, 5B.

The retention member 1 comprises a base element 10 having a generally triangular shape with three tips and three legs extending in between the tips of substantially equal length. The retention member 10 has a top side 104 for receiving the catheter 2 and a bottom side 103 to be placed on the skin of a patient P.

Figure 3:
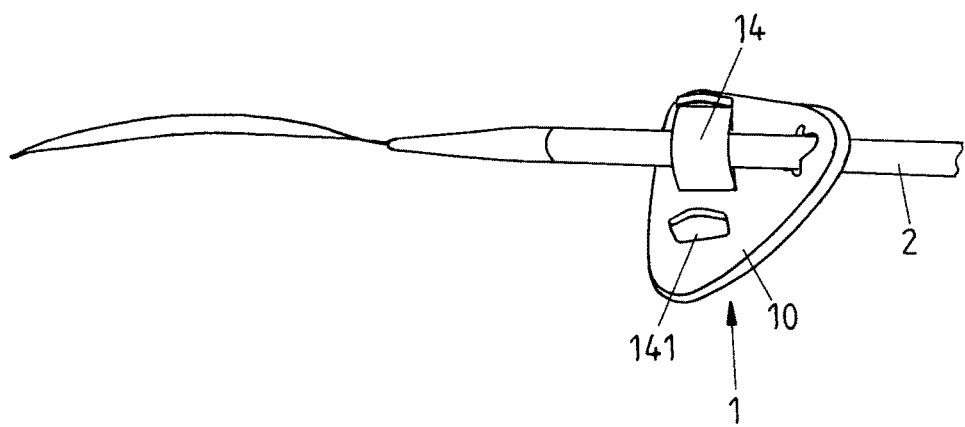
FIG. 3 shows a view of the retention member, with a catheter being placed on the retention member.

The retention member 1 comprises a ribbon 14 connected, at a first end 140, to the top side 104 of the base element 10 and having a second end 141 opposite the first end 140. The ribbon 14 extends from the base element 10 and can be inserted through openings 150, 151 formed in the base element 10 in order to secure the catheter 2 on the retention member 1, as it is illustrated in FIG. 3.

The openings 150, 151 are formed by slits in the base element 10, wherein the slits are terminated at both ends by end holes 150A, 151A extending from the top side 104 through to the bottom side 103 of the base element 10. The ribbon 14 can be inserted through the slits 150, 151 (leading to an elastic deformation of the base element 10 in the area of the slits 150, 151). The end holes 150A, 151A ensure that the base element 10 is not torn open in the area of the slits 150, 151 when using the retention member 1.

Figure 2:
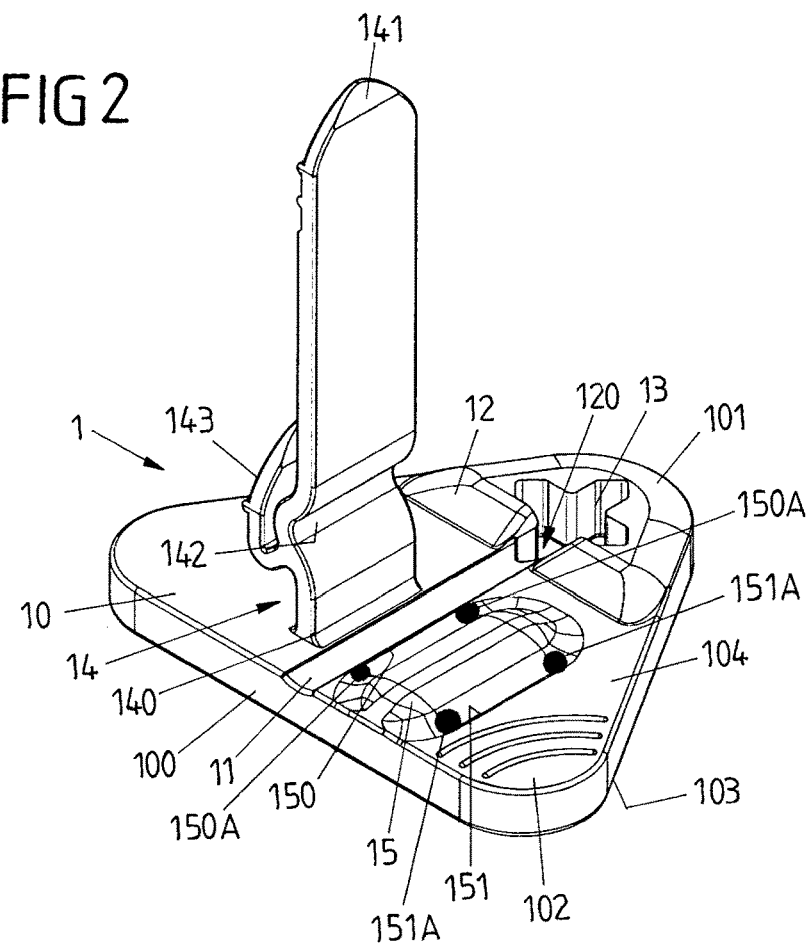
FIG. 2 shows a perspective view of an embodiment of a retention member for securing a catheter on a patient.

The base element 10, at its top side 104, comprises a groove 11 extending along a middle line of the base element 10 from a leg 100 in between a first end a second tip of the triangular base element 10 towards a third tip 101 of the base element 10, as it is visible in FIG. 2. The groove 11 is formed into the top side 104 of the base element 10 and passes by the ribbon 14, such that by inserting the ribbon 14 with its second end 141 through the openings 150, 151 a loophole is formed through which the catheter 2 may extend for securing it to the retention member 10 (see the sectional views of FIGS. 4B, 4C and 5A, 5B).

At the third tip 101 a guide hole 13 is formed having a cross-sectional shape of a cross. The guide hole 13 reaches from the top side 104 of the base element 10 towards the bottom side 103 and allows to insert the catheter 2 such that the catheter 2 extends along the groove 11 on the top side 104 and reaches through the guide hole 13 to pass from the top side 104 to the bottom side 104 of the base element 10.

The guide hole 13, as said, is arranged at the third tip 101 of the base element 10. The region of the guide hole 13 herein is separated from the region of the base element 10 in which the ribbon 14 is placed by means of a wall section 12 protruding from the top side 104 of the base element 10, the wall section 12 extending transversely with respect to the middle line, i.e., transversely to the groove 11 formed on the top side 104 of the base element 10. The wall section 12 provides for a stiffening across the base element 10 and allows for a bending of the tip 101 carrying the guide hole 13 about the wall section 12, the wall section 12 providing for a bending axis, as it is illustrated in FIG. 3.

By inserting the catheter 2 through the guide hole 13 from the top side 104 of the base element 10 towards the bottom side 103 and by, at least to some extent, bending the base element 10 at the third tip 101, the catheter 2, at the tip 101, is (slightly) bent and pretensioned towards the skin of the patient P such that it is pressed against the skin and assumes a defined, secure position on the skin of the patient P.

For securing the catheter 2 on the retention member 1, the ribbon 14, with its second end 141, is inserted through the openings 150, 151 formed in the base element 10. Herein it is possible to first place the catheter 2 on the base element 10 and to insert the ribbon 14 through the openings 150, 151 after placing the catheter 2 on the base element 10. It however is also possible to first insert the ribbon 14 through the openings 150, 151 to form a loophole and to subsequently insert the catheter 2 through the loophole formed by the ribbon 14.

Figure 4A:
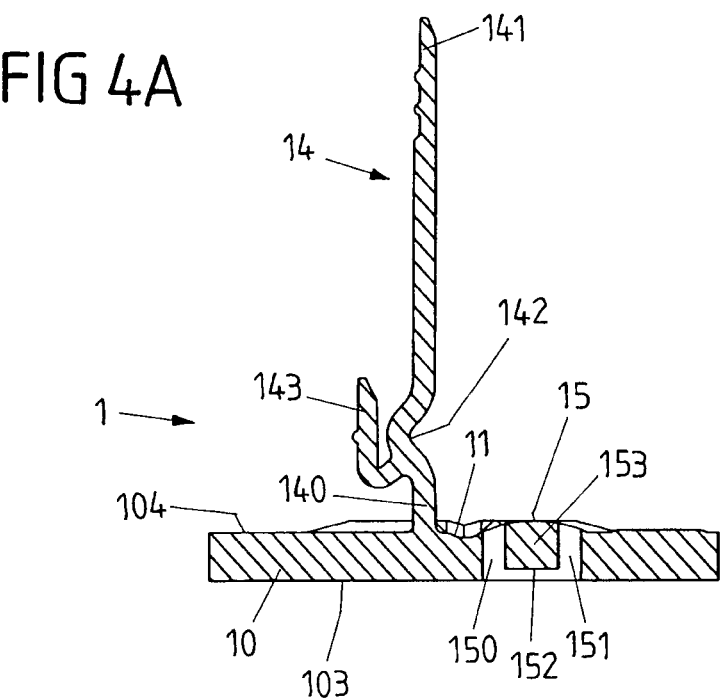
FIG. 4A shows a sectional view of the retention member, in a relaxed state of the ribbon of the retention member.
Figure 4B:
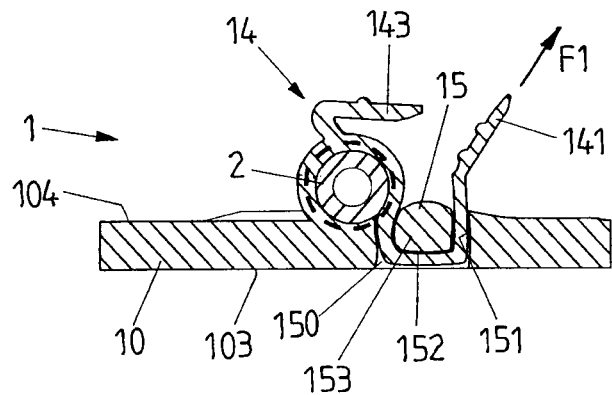
FIG. 4B shows a sectional view of the retention member, with a catheter being placed on the retention member.
Figure 4C:
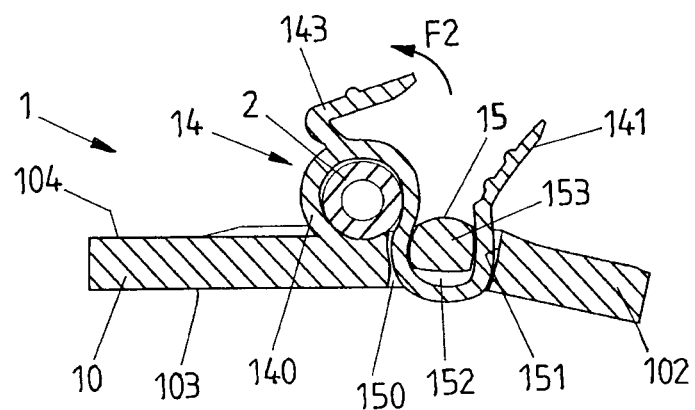
FIG. 4C shows a sectional view of the retention member, when releasing the ribbon to remove the catheter from the retention member.

As visible from the sectional views of FIGS. 4B and 4C, the ribbon 14, when inserted through the openings 150, 151, extends about a rib 153 formed in between the openings 150, 151. The ribbon 14 herein extends through a first opening 150 from the top side 104 of the base element 10 towards the bottom side 103, reaches around the rib 153 and extends back from the bottom side 103 towards the top side 104 through a second opening 151. By pulling on the second end 141 of the ribbon 14 in a pulling direction F1 as indicated in FIG. 4B, a catheter 2 extending through the loophole formed by the ribbon 14 can be fastened to the base element 10 such that it is securely held on the base element 10.

As it is visible for example from FIG. 4A, a bottom side 152 of the rib 153 is recessed with respect to the bottom side 103 of the base element 10. This allows to place the ribbon 14 around the rib 153, as it is shown in FIG. 4B, without the ribbon 14 protruding beyond the bottom side 103 of the base element 10 when the ribbon 14 is inserted through the openings 150, 151.

To stiffen the base element 10 in the region of the rib 153, an elevation 15 is formed within the region of the rib 153, the elevation 15 protruding from the top side 104 of the base element 10.

When the ribbon 14 is inserted through the openings 150, 151 and when the ribbon 14 is tightened by pulling on the second end 141 to securely fasten a catheter 2 on the base element 10, the ribbon 14 is held in place by compressional forces acting in between the ribbon 14 and the base element 10 within the openings 150, 151 such that the ribbon 14 is frictionally retained within its inserted position.

For releasing the catheter 2, a user may grab on a pulling handle 143 arranged on a section of the ribbon 14 in between the first end 140 and the second end 141. By pulling, in a pulling direction F2 (see FIG. 4C), on the pulling handle 143 the ribbon 14 can be pulled out of the openings 150, 151 such that the loophole formed by the ribbon 14 may be opened to remove the catheter 2 from the retention member 1. At the same time a user may press onto a tip 102 of the base element 10 closest to the rib 153 formed in between the openings 150, 151, such that a pulling force in the direction F2 may be exerted onto the ribbon 14 in an easy manner.

The retention member 1 with the base element 10 and the ribbon 14 formed thereon is integrally formed in one piece for example from silicone rubber. The retention member 1 is easy and intuitive to handle and at the same time is easy and cost-efficient to manufacture.

Figure 5A:
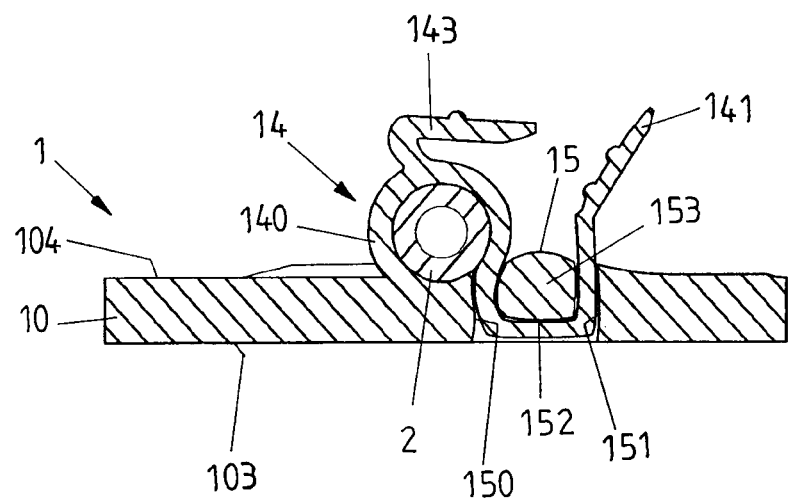
FIG. 5A shows a sectional view of the retention member, with a catheter of a first diameter being placed on the retention member.
Figure 5B:
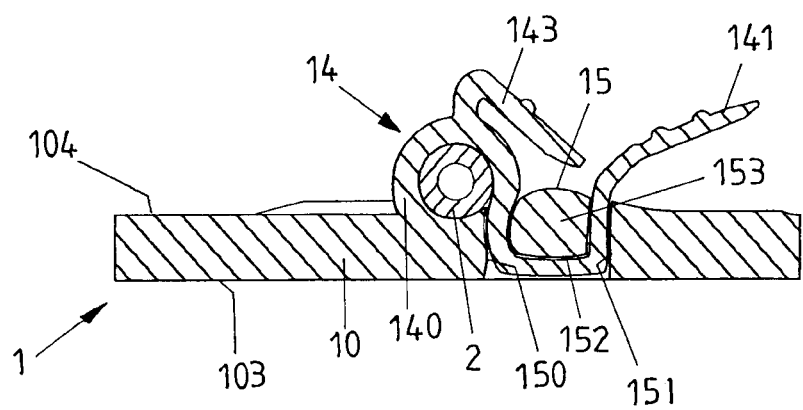
FIG. 5B shows a sectional view of the retention member, with a catheter of a second, smaller diameter being placed on the retention member.

In addition, the retention member 1 may be, as illustrated in FIGS. 5A and 5B, used in connection with catheters 2 of different diameters, without having to modify the retention member 1. In particular, by placing a catheter 2 of a particular diameter on the base element 10 of the retention member 1 and by suitably pulling on the second end 141 of the ribbon 14 until the catheter 2 is securely fastened to the base element 10, a catheter 2 of any (conventionally used) diameter may be fastened to the retention member 1 without having to structurally modify the retention member 1.

Figure 6:
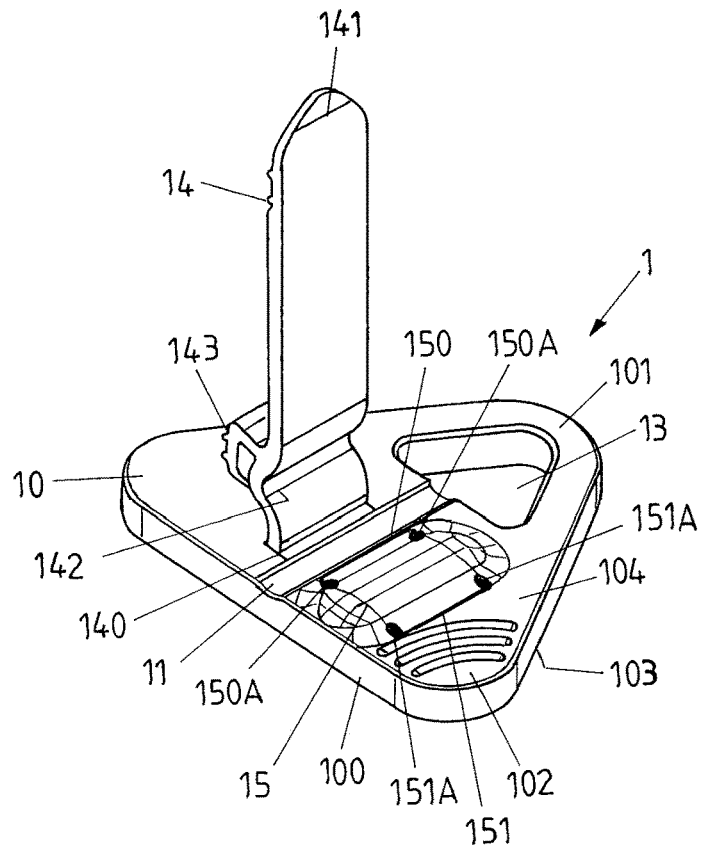
FIG. 6 shows a perspective view of another embodiment of a retention member for securing a catheter on a patient.
Figure 7:
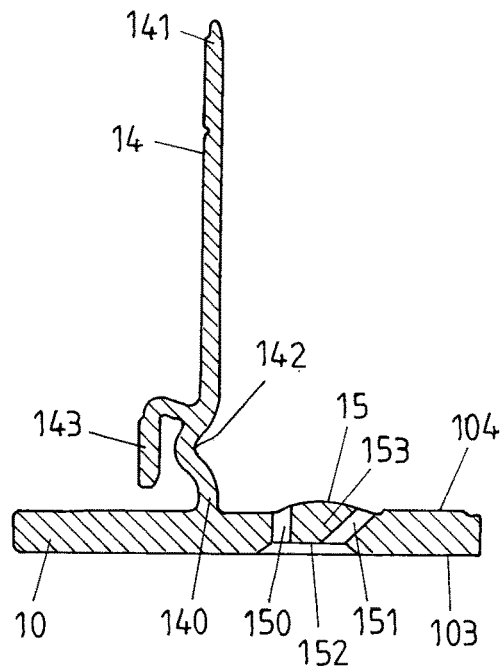
FIG. 7 shows a sectional view of the retention member, in a relaxed state of the ribbon of the retention member.

FIGS. 6 and 7 show another embodiment of a retention member 1 having a base element 10 and a ribbon 14 connected thereto.

The embodiment of FIGS. 6 and 7 differs from the previously described embodiment in the shape of the guide hole 13, the shape of the pulling handle 143 attached to the ribbon 14 and furthermore in the shape of the opening 151 extending through the base element 10. Furthermore, the embodiment of FIGS. 6 and 7 does not comprise a wall 12 protruding from the base element 10 to structurally separate the area of the guide hole 13 from the area of the base element 10 to which the ribbon 14 is attached.

In the embodiment of FIGS. 6 and 7, the guide hole 13 has a triangular shape.

Analogously as depicted in FIG. 3 a catheter 2 may be inserted through the guide hole 13 to extend along a groove 11 on the top side 104 of the base element 10 through the guide hole 13 towards the bottom side 103 of the base element 10. This allows for a guiding of the catheter 2 and a pretensioning of the catheter 2 towards the patient's skin.

The pulling handle 143 in the embodiment of FIGS. 6 and 7 points towards the other side as compared to the embodiment of FIG. 2 to 5A, 5B. Just as well the pulling handle 143 allows a user to pull on the ribbon 14 in order to release the ribbon 14 with its and 141 from the base element 10.

As visible in the sectional view of FIG. 7, the opening 151 extends through the base element 10 at a tilted angle. Again, as in the embodiment of FIG. 2 to 5A, 5B, the ribbon 14 with its end 141 may be inserted through the openings 150, 151 formed by slits in the base element 10 and terminated by end holes 150A, 151A such that, in a closed state analogously to FIG. 4B, a loophole is formed to fasten the catheter 2 on the base element 10.

Other than that the embodiment of FIGS. 6 and 7 resembles the embodiment of FIG. 2 to 5A, 5B, such that it also shall be referred to the detailed description above.

The idea underlying the invention is not limited to the embodiments described above, but may be implemented in an entirely different manner.

A retention member of the kind described herein may be employed for different purposes, for example for the medication, hydration or feeding of a patient. The gastro-intestinal feeding of a patient in this regard is only one example of a possible use of a retention member as described herein.

The retention member may have a different shape and structure than described herein. For example, the retention member may be made out of a different material than silicone rubber. In addition, the retention member may have a shape different than a triangular shape, for example a quadratic or rectangular shape.

LIST OF REFERENCE NUMERALS

1 Retention member
10 Base element
100 Leg
101, 102 Tip
103 Bottom side
104 Top side 11 Groove
12 Wall
120 Opening
13 Guide hole
14 Ribbon
140, 141 End
142 Reception groove
143 Pulling handle
15 Elevation
150, 151 Opening
150A, 151A End hole
152 Bottom side
153 Rib
2 Catheter
F1, F2 Direction
P Patient

The invention claimed is:

1. Retention member (1) for securing a catheter (2) on a patient (P), comprising:
   a base element (10) having a bottom side (103) and a top side (104), the bottom side being placeable on the patient (P) and the top side (104) being adapted for receiving the catheter (2),
characterized by
   a ribbon (14) having a first end (140) connected to the top side (104) of the base element (10) and having a second end (141) opposite the first end (140), wherein the base element (10) comprises at least one opening (150, 151) through which the second end (141) of the ribbon (14) is insertable for fixing the catheter (2) on the retention member (1) in between the base element (10) and the ribbon (14), the base element (10) further comprising a first opening (150) and a second opening (151) separated by a rib (153), the ribbon (14) being insertable through the first opening (150), and the second opening (151) to extend about the rib (153), and the rib (153), at its side opposite the top side (104) of the base element (10), being recessed with respect to the bottom side (103) of the base element (10).

2. Retention member (1) according to claim 1, characterized in that the retention member (1) is integrally formed in one piece.

3. Retention member (1) according to claim 1, characterized by an elevation (15) placed on the top side (104) of the base element (10) in between the first opening (150) and the second opening (151) and protruding from the top side (104) of the base element (10).

4. Retention member (1) according to claim 1, characterized in that the base element (10) has a generally triangular shape.

5. Retention member (1) according to claim 4, characterized in that the guide hole (13) is arranged at a tip (101) of the generally triangular base element (10).

6. Retention member (1) according to claim 1, characterized in that the base element (10) comprises a groove (11) extending along the top side (104) for receiving the catheter (2), the ribbon (14) bridging over the groove (11) when inserted into the at least one opening (150, 151).

7. Retention member (1) according to claim 1, characterized in that the base element (10) comprises a guide hole (13) extending through the base element (10) from the top side (104) to the bottom side (103).

8. Retention member (1) according to claim 7, characterized by a wall section (12) placed on the top side (104) of the base element (10) and extending across the top side (104), the guide hole (13) being placed on a first side of the wall section (12) and the ribbon on another, second side of the wall section (12).

9. Retention member (1) according to claim 8, characterized in that the wall section (12) comprises an opening (120) forming a passage for the catheter (2) from the second side towards the guide hole (13) on the first side of the wall section (12).

10. Retention member (1) according to claim 8, characterized in that the base element (10) is bendable about the wall section (12).

11. Retention member (1) according to claim 1, characterized in that the ribbon (14), in a state in which it is not inserted into the at least one opening (150, 151), comprises a reception groove (142) formed by a curvature of the ribbon (14).

12. Retention member (1) according to claim 1, characterized in that the ribbon (14), at a section in between the first end (140) and the second end (141), comprises a pulling handle for pulling the ribbon out the at least one opening (150, 151).

13. Retention member (1) for securing a catheter (2) on a patient (P), comprising:
   a base element (10) having a bottom side (103) and a top side (104), the bottom side being placeable on the patient (P) and the top side (104) being adapted for receiving the catheter (2),
characterized by
   a ribbon (14) having a first end (140) connected to the top side (104) of the base element (10) and having a second end (141) opposite the first end (140), wherein the base element (10) comprises at least one opening (150, 151) through which the second end (141) of the ribbon (14) is insertable for fixing the catheter (2) on the retention member (1) in between the base element (10) and the ribbon (14), the base element (10) comprising a guide hole (13) extending through the base element (10) from the top side (104) to the bottom side (103), and a wall section (12) placed on the top side (104) of the base element (10) and extending across the top side (104), the guide hole (13) being placed on a first side of the wall section (12) and the ribbon on another, second side of the wall section (12).

14. Retention member (1) according to claim 13, characterized in that the retention member (1) is integrally formed in one piece.

15. Retention member (1) according to claim 13, characterized in that the base element (10) comprises a first opening (150) and a second opening (151) separated by a rib (153), the ribbon (14) being insertable through the first opening (150) and the second opening (151) to extend about the rib (153).

16. Retention member (1) according to claim 15, characterized in that the rib (153), at its side opposite the top side (104) of the base element (10), is recessed with respect to the bottom side (103) of the base element (10).

17. Retention member (1) according to claim 13, characterized by an elevation (15) placed on the top side (104) of the base element (10) in between the first opening (150) and the second opening (151) and protruding from the top side (104) of the base element (10).

18. Retention member (1) according to claim 13, characterized in that the base element (10) has a generally triangular shape.

19. Retention member (1) according to claim 13, characterized in that the base element (10) comprises a groove (11) extending along the top side (104) for receiving the catheter (2), the ribbon (14) bridging over the groove (11) when inserted into the at least one opening (150, 151).

20. Retention member (1) according to claim 18, characterized in that the guide hole (13) is arranged at a tip (101) of the generally triangular base element (10).

\* \* \* \* \*